United States Patent
Binz et al.

(10) Patent No.: US 6,576,047 B2
(45) Date of Patent: Jun. 10, 2003

(54) SEPARATION COLUMN FOR ANALYZING GASES

(75) Inventors: Dieter Binz, Hirschberg (DE); Albrecht Vogel, Stutensee (DE); Erwin Barsch, Ladenburg (DE); Christian J. Schmidt, Heidelberg (DE)

(73) Assignee: ABB Patent GmbH, Ladenburg (DE)

( * ) Notice: Subject to any disclaimer, the term of this patent is extended or adjusted under 35 U.S.C. 154(b) by 0 days.

(21) Appl. No.: 10/045,768

(22) Filed: Jan. 10, 2002

(65) Prior Publication Data

US 2002/0100368 A1 Aug. 1, 2002

(30) Foreign Application Priority Data

Jan. 10, 2001 (DE) .......................................... 101 00 921

(51) Int. Cl.[7] .............................................. B01D 15/08
(52) U.S. Cl. ............................. 96/101; 96/105; 96/106
(58) Field of Search .................................... 96/101–107

(56) References Cited

U.S. PATENT DOCUMENTS

| | | | | |
|---|---|---|---|---|
| 3,149,941 A | * | 9/1964 | Barnitz et al. ................. | 96/101 |
| 3,283,483 A | * | 11/1966 | Halasz et al. ................. | 96/101 |
| 3,522,172 A | | 7/1970 | Pretorius et al. | |
| 3,630,006 A | * | 12/1971 | Sandoval ..................... | 96/101 |
| 3,662,520 A | * | 5/1972 | Saunders .................. | 96/105 X |
| 3,796,657 A | * | 3/1974 | Pretorius et al. .......... | 96/101 X |
| 4,208,284 A | * | 6/1980 | Pretorius et al. .......... | 96/101 X |
| 4,399,032 A | * | 8/1983 | Mott ......................... | 96/106 X |
| 4,935,040 A | * | 6/1990 | Goedert ..................... | 96/104 X |
| 4,951,503 A | | 8/1990 | Fini | |
| 6,454,840 B1 | * | 9/2002 | Gellert et al. .................. | 96/101 |

FOREIGN PATENT DOCUMENTS

| | | | | |
|---|---|---|---|---|
| DE | 44 35 015 A1 | | 3/1996 | |
| GB | 1399397 A | * | 7/1975 | ................. 96/106 |
| WO | WO 94/12432 | | 6/1994 | |

OTHER PUBLICATIONS

Esther Forgács et al.: "Retention strength and selectivity of porous graphitized carbon columns—Theoretical aspects and practical applications", Trends in Analytical Chemistry, vol. 14, 1995, No. 1, pp. 23–28.

* cited by examiner

Primary Examiner—Robert H. Spitzer
(74) Attorney, Agent, or Firm—Laurence A. Greenberg; Werner H. Stemer; Ralph E. Locher

(57) ABSTRACT

A separation column for analyzing a gas includes a capillary which is filled with a separation material. In order to be able to use the separation column in a microsystem technology, spheres are used as the separation material. The spheres all have the same diameter. The diameters of the spheres are slightly smaller than the internal diameter of the capillary or are matched to the internal diameter of the capillary. The spheres are provided inside the capillary in a row one behind the other.

10 Claims, 4 Drawing Sheets

SEPARATION COLUMN FOR ANALYZING GASES

BACKGROUND OF THE INVENTION

FIELD OF THE INVENTION

The invention relates to a separation column for analyzing gases.

Separation columns are for example used for analyzing natural gas and for determining the calorific value of the natural gas. A separation column which is configured as a capillary is already known. The capillary is filled with a carrier material in the form of spheres which are made from carbon and have a diameter of 150 $\mu$m to 200 $\mu$m. The separation column has a diameter of a few millimeters and a length of several meters. This separation column can be used to separate the inert gases contained in the natural gas from the fractions which have a calorific value, so that it is possible to determine the calorific value of the gas which is to be analyzed. Five minutes are required to carry out the measurement, and during this period approximately 15 ml of carrier gas have to be passed through the separation column per second.

Separation columns are in increasing demand in microtechnology in order to carry out a rapid analysis of gases. The separation column described above is much too large to be used for this application. In addition, too much time is required for the analysis of a gas. Moreover, for devices with dimensions in the millimeter range, which require a suitable separation column, it is not possible to provide relatively large quantities of carrier gas for every analysis.

SUMMARY OF THE INVENTION

It is accordingly an object of the invention to provide a separation column which overcomes the above-mentioned disadvantages of the heretofore-known separation columns of this general type and which has dimensions such that the separation column can be integrated in any device used in microtechnology while also being able to individually separate natural gas into all its constituents, so that its calorific value can be determined therefrom.

With the foregoing and other objects in view there is provided, in accordance with the invention, a separation column for analyzing gases, including:

a capillary having an inner diameter;

spheres having substantially identical diameters, the spheres being disposed as a separation material in the capillary; and each of the substantially identical diameters of the spheres being matched to the inner diameter of the capillary or being marginally smaller than the inner diameter of the capillary.

According to another feature of the invention, the spheres are made of carbon or Carbosphere carbon.

According to yet another feature of the invention, the inner diameter of the capillary is substantially 200 $\mu$m, and the substantially identical diameters of the spheres are between 150 $\mu$m and 200 $\mu$m.

According to another feature of the invention, the spheres are disposed inside the capillary such that all of the center points of the spheres are provided along a straight line.

According to a further feature of the invention, an inert powder is provided between the spheres at least in given regions inside the capillary.

According to another feature of the invention, the inert powder is made from carbon, Buckminister Fullerene $C_{60}$ or Carbosphere carbon.

According to another feature of the invention, a respective gas-permeable closure is provided at each of the two ends of the capillary.

According to yet another feature of the invention, the inner diameters of two further capillaries are slightly smaller than the substantially identical diameters of the spheres, and the outer diameters of the two further capillaries are matched to the inner diameter of the capillary. The two further capillaries each have a respective first end inserted in a respective one of the two ends of the capillary, the two further capillaries being connected to the capillary in a gastight and permanent manner such that the two further capillaries form gas-permeable closures at the two ends of the capillary.

According to a further feature of the invention, a support element includes a plate and a cover, the plate and the cover being made from glass or silicon. The plate has a surface and has a channel formed in the surface, the channel having relatively wider sections for receiving the spheres and the channel having relatively narrower sections in front of and behind each of the relatively wider sections. The cover closes off the channel in a gastight manner with respect to an outside environment for providing the capillary, the channel having an end serving as an inlet opening for a carrier gas and a sample gas.

According to another feature of the invention, a support element includes a plate and a cover, the plate and the cover being made from glass or silicon. The plate and the cover have respective surfaces facing one another and have a channel formed partially in each of the surfaces, the channel having relatively wider sections for receiving the spheres and the channel having relatively narrower sections in front of and behind each of the relatively wider sections. The cover closes off the channel in a gastight manner with respect to an outside environment for providing the capillary. One end of the channel serves as an inlet opening for a carrier gas and a sample gas or test gas.

The separation column according to the invention is configured as a thin capillary. Its length is approximately 30 mm and its internal diameter is 150 $\mu$m to 200 $\mu$m. It is filled with a separation material made from carbon. The carbon is in the form of spheres with a diameter of between 150 $\mu$m and 180 $\mu$m. If the diameter of the spheres is selected to be greater than this, the distance between the internal diameter of the capillary and the spheres becomes too small. The separation column then becomes very sensitive to bending stresses and may break. To enable natural gas to be sufficiently separated into all its constituents, the spheres made from carbon have to be provided in a very specific form within the capillary. Optimum operation of the separation column according to the invention is achieved if all the spheres are provided in a row one behind the other, so that there are no spheres positioned next to one another, but rather each sphere is provided individually along the axis of the capillary. The result of this structure is that the natural gas is separated into the constituents methane, carbon dioxide, nitrogen, helium, hydrogen sulphide and arsenic compounds, as well as higher molecular hydrocarbons, such as ethane, propane, isobutane, butane and hexane, provided that all these constituents are contained in the natural gas.

To ensure that the spheres are held permanently in the capillary, a gas-permeable closure is provided at each of the two ends of the capillary. Preferably, each of the closures is formed by a capillary, the internal diameter of which is smaller than the diameter of the spheres and one end of which is fitted into the end of the separation column and is connected in a gastight manner thereto. An adhesive in the form of epoxy resin is preferably used to connect the closures to the separation column. Since the two closures at the ends of the separation columns are configured as capillaries, it is possible for the gas which is to be analyzed and also the carrier gas to be introduced into the separation column without problems. Moreover, the components or eluents into which the gas which is to be analyzed is separated in the separation column, and also the carrier gas, can escape without difficulty from the second end of the separation column.

The maximum separation capacity of the separation column, i.e. its highest plate number, is achieved at a flow of approximately 5 μl/sec if hydrogen is used as carrier gas. Natural gas is separated into the constituents $CO_2$, methane and air in less than 16 sec if the temperature is increased from 0° C. to approximately 50° C. in this time period.

The flow rate range of high plate number can be widened downward if an inert powder in the form of Buckminister Fullerene $C_{60}$ is positioned between the individual spheres of carbon. Instead of this powder, it is also possible to use a carbon powder, which is also used to produce the spheres described above. A powder made from Carbosphere carbon is also suitable for this purpose.

An addition of such a powder reduces the flow through the separation column. However, if the flow rate along the active surfaces of the separation column which is filled with spheres and an inert powder is to be maintained at the same level in order to obtain the maximum number of plates, the overall flow through the capillary is to be reduced.

Because of the inert powder which fills the spaces between the carbon spheres, there are numerous different ways for the gases to flow through the separation column past the spheres. Because of these measures, the number of plates is independent within wide ranges, over virtually an order of magnitude, of the overall flow through the separation column or the admission pressure of the carrier gas. It is therefore possible, for the separation column according to the invention, for the flow to be set according to other, independent criteria while maintaining the number of plates. One such criterion may, for example, be a defined flow which requires an additional separation column or another component connected upstream of the separation column according to the invention.

As mentioned above, the separation column according to the invention is provided for use in microsystems technology. Therefore, the separation column may also be formed directly in a support element, through the use of which a large number of Microsystems technology components can be combined to form a single unit. Support elements of this type are provided with a plate and a cover made from glass or silicon. The cover delimits the surface of the plate in a gastight manner with respect to the outside. For the separation column, a channel is formed in the surface of the plate. The channel is provided with widened sections, the diameters of which are slightly larger than the diameters of the carbon spheres. Then, a sphere of carbon is provided in each widened section of the channel. In front of and behind each widened section, the channel is narrowed to a diameter which is no greater than the inlet opening of the channel. The result is that the spheres provided in the widened sections are held in place. In the region of the widened sections, the diameter of the channel is no greater than the internal diameter of the capillary described above. The channel is also of the same length as the capillary. After the spheres have been provided in the channel, the cover is connected to the surface of the plate in such a way that the channel is closed off in a gastight manner.

It is also possible for the channel to be formed partially in the cover and partially in the surface of the plate. In this case, at the locations at which in each case one sphere is to be provided in the channel, the cover is likewise provided with a deeper recess, the channel in this case too being narrowed in front of and behind each widened section. Therefore, in this way too it is possible to form a separation column as described above. Forming the separation column partially in the cover and partially in the plate has the advantage that the recesses in either the plate or the cover do not have to be as deep as if the separation column is formed only in the surface of the plate. Consequently, the cover and the plate can be of thinner configuration. The first end of the separation column is open so that a gas which is to be analyzed and carrier gas can be introduced into the channel. The second end of the channel may be connected to a detector, which may likewise be provided in a recess in the plate.

Other features which are considered as characteristic for the invention are set forth in the appended claims.

Although the invention is illustrated and described herein as embodied in a separation column for the analysis of gases, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
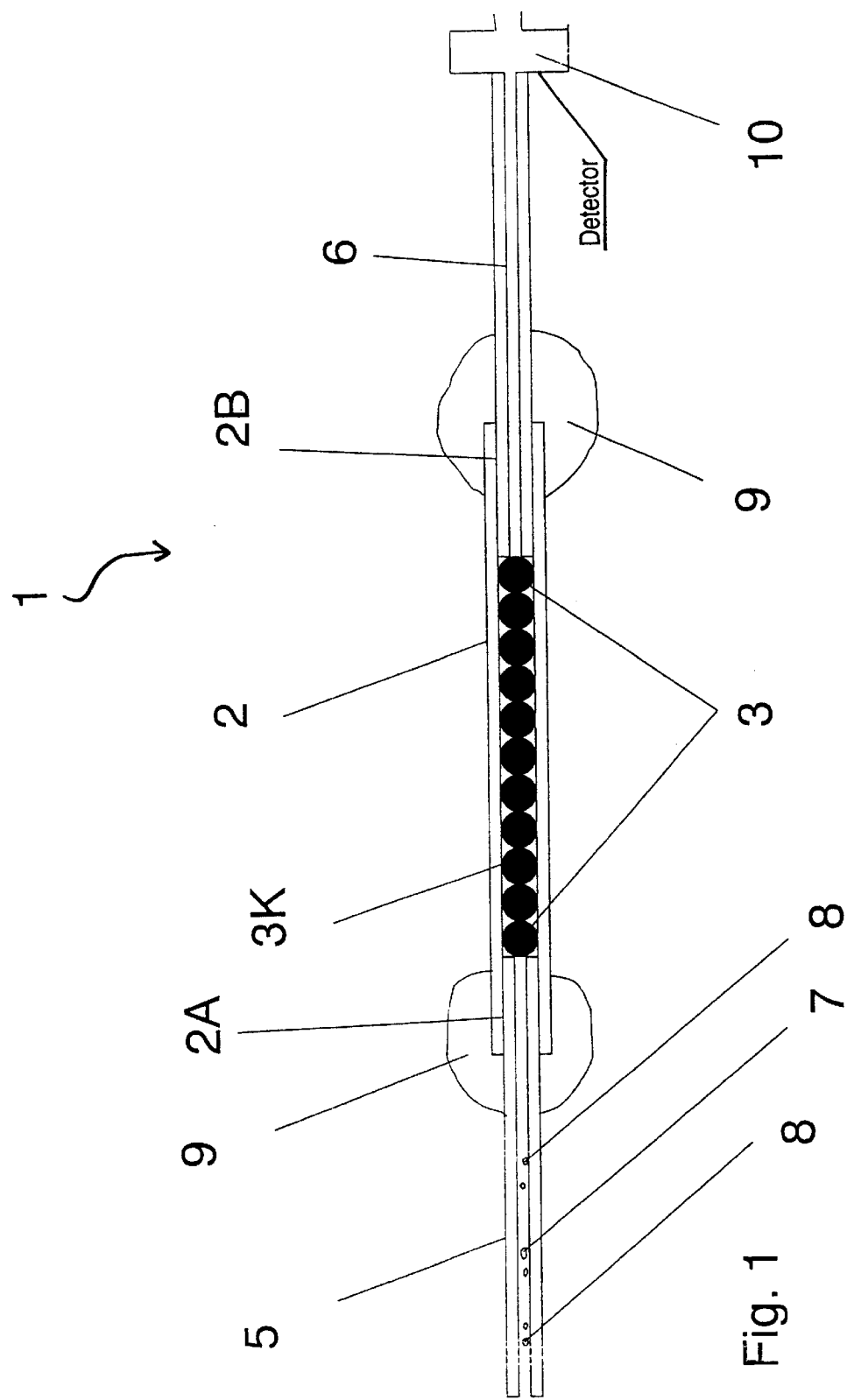
FIG. 1 is a diagrammatic sectional view of a separation column according to the invention.

Referring now to the figures of the drawings in detail and first, particularly, to FIG. 1 thereof, there is shown a separation column 1 according to the invention. The separation column 1 substantially includes a capillary 2, separation material 3 and two gas-permeable closures 5 and 6. The capillary 2 forms the core of the separation column 1. It is made from quartz glass which is coated with polyimide. In the exemplary embodiment shown here, its length is 30 mm. In addition, it has an internal diameter of 200 μm. The separation material 3 is provided in the interior of the capillary 2. The separation material is embodied as particles 3K which are in the form of spheres. The spheres 3K have a diameter which is 150 μm to 200 μm. The diameter is preferably selected to be slightly less than 200 μm, since otherwise an excessive bending stress acts on the separation column 1, and consequently the column may break. The spheres 3K are made from carbon or Carbosphere carbon.

They are provided in the capillary 2 in such a way that all the spheres 3K are provided one behind the other, so that their center points lie approximately in the longitudinal axis of the separation column 1. At both ends 2A and 2B, the capillary 2 is provided with in each case one closure 5 and 6. Both closures 5 and 6 are of the same dimensions and are configured as capillaries. The dimensions of the capillaries 5 and 6 are selected in such a way that their external diameters correspond to or are slightly smaller than the internal diameter of the capillary 2. The internal diameter of the capillaries 5 and 6 is such that it is at any rate slightly smaller than the external diameter of the spheres 3K. In each case one end of the capillaries 5 and 6 is fitted into end 2A, 2B of the capillary 2. In addition, both capillaries 5 and 6 are connected to the capillary 2 in a permanent and gastight manner. They are preferably attached to the ends 2A and 2B through the use of an adhesive 9 which is based on epoxy resin. With the aid of these two closures 5 and 6, it is possible for a carrier gas 7 and a sample gas 8, for example natural gas, to be introduced into the capillary 2. At the same time, it is ensured that the carrier gas 7 and the components of the natural gas 8 which are to be separated with the aid of the separation material 3 also leave the capillary 2 without the spheres 3 being flushed out. In the exemplary embodiment illustrated here, a detector 10 is connected to the second end 2B of the separation column 1. On account of the time order in which the components of the sample gas 8 leave the separation column 1, it is possible to determine which components are contained in the sample gas which is to be analyzed. Each component of the sample gas changes the electrical resistance of a wire provided in the interior of the detector. The extent of this change is dependent on the proportion of the overall mix of the gas to be analyzed which is made up by each component. Then, by way of example, the calorific value of the natural gas 8 which has been analyzed can be determined from this information.

Figure 2:
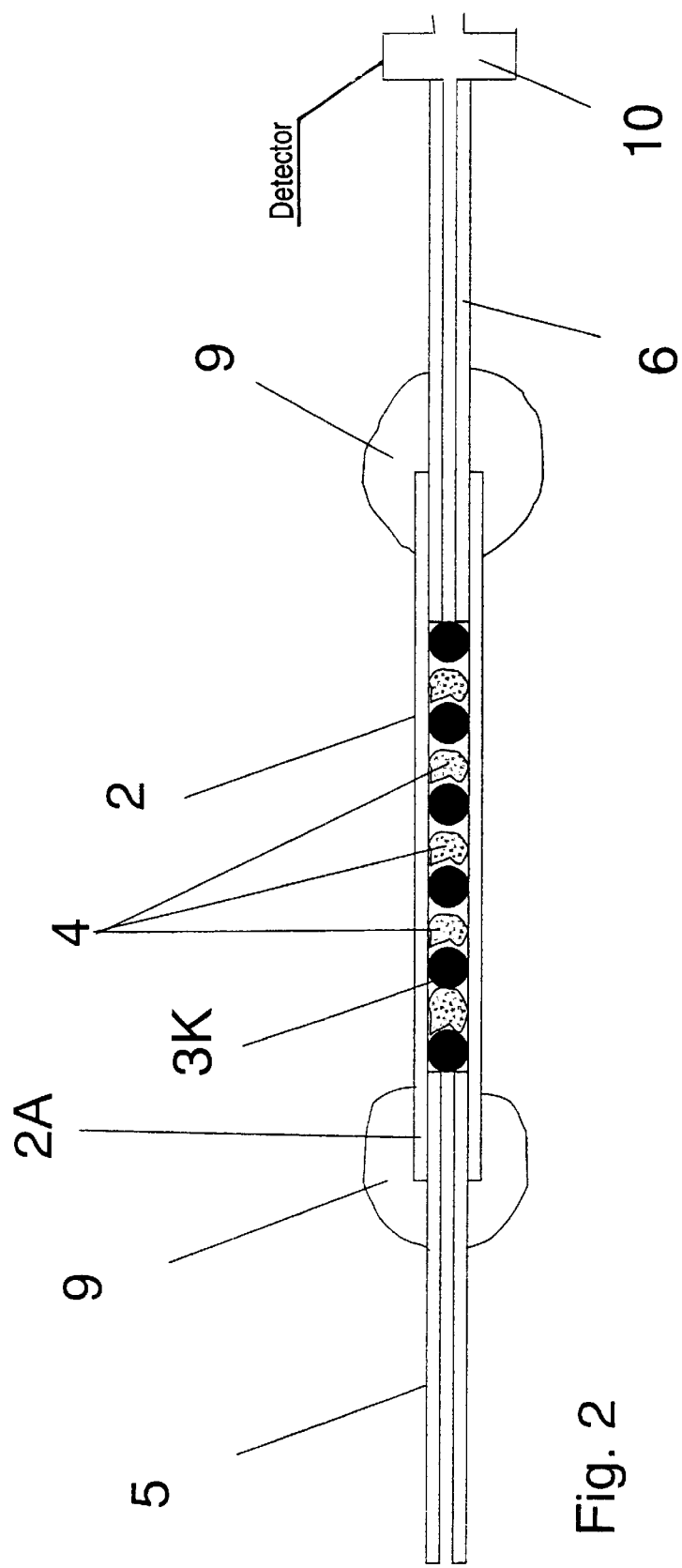
FIG. 2 is a diagrammatic sectional view of a variant of the separation column illustrated in FIG. 1.

The embodiment of the separation column 1 according to the invention which is illustrated in FIG. 2, differs from the separation column 1 which is illustrated in FIG. 1 and has been explained in the associated description only in that the capillary 2, as well as the spheres 3K, is also filled with an inert powder 4. Therefore, identical components are provided with identical reference symbols. The inert powder 4 is provided between each pair of successive spheres 3K. The powder may be formed of Buckminister Fullerene $C_{60}$. Instead of this powder, it is also possible to use a powder made from carbon which is used to produce the spheres described above.

Figure 3:
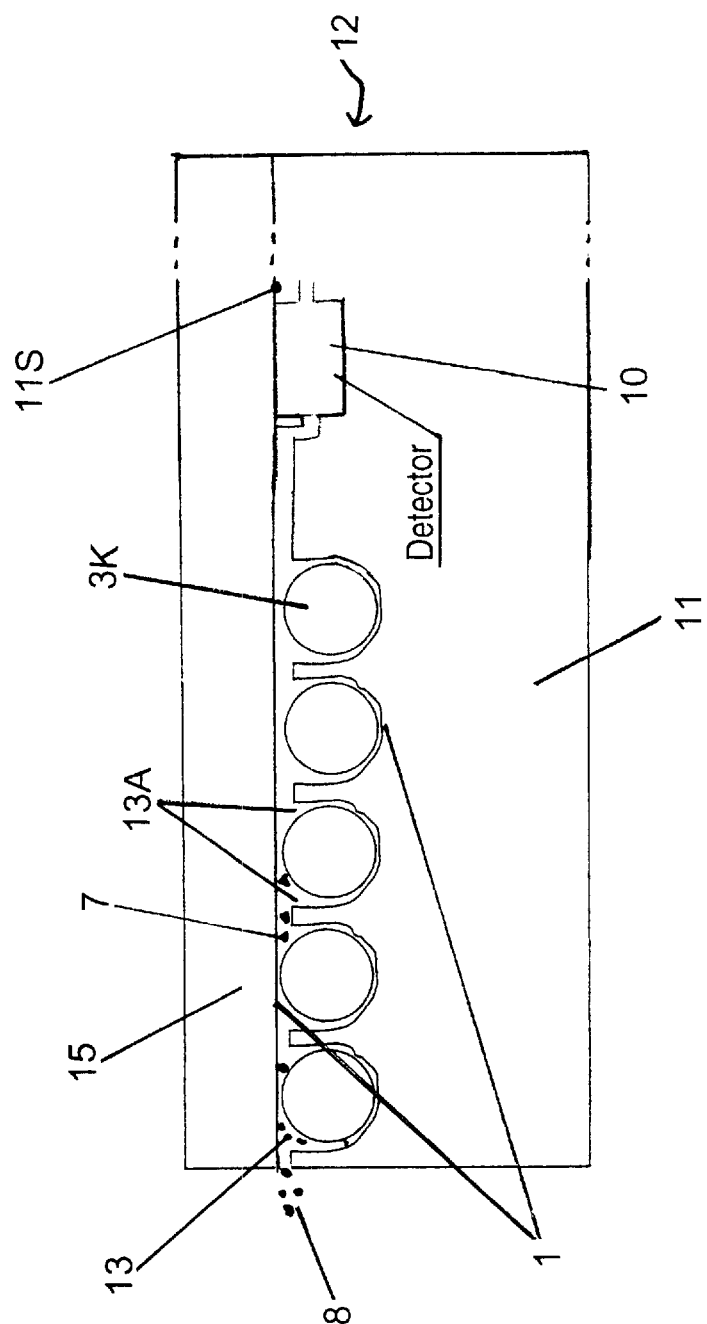
FIG. 3 is a diagrammatic sectional view of a separation column according to the invention which is integrated in a support element.

As shown in FIG. 3, the separation column 1 may also be formed directly within a support element in which further components used in microsystems technology can also be integrated. For this purpose, a channel 13 of a length of, for example, 30 mm is formed into the surface 11S of a plate 11 which is part of the support element 12. A widened section 13A is formed at the locations at which a sphere 3K of carbon is to be provided in the channel 13. The diameter of each widened section 13A is slightly greater than the diameter of the spheres 3K, so that a carrier gas 7 and a sample gas 8 can flow around and past the sphere 3K. In front of and behind each widened section 13A, the channel 13 is narrowed in such a way that it is still possible for the carrier gas 7 and the sample gas 8 to flow through. The narrowing of the channel 13 in front of and behind the widened sections 13A ensures that the spheres 3K are held in their predetermined position. A sphere 3K of carbon is provided in each widened section 13A of the channel 13. Then, a cover 15 made from glass or silicon is provided on the surface 11S of the plate 11 and is connected to the plate 11 in such a way that the entire surface 11S of the plate 11 is closed off in a gastight manner. The first end of the separation column 1 is sufficiently wide open such that it is possible for the carrier gas 7 and the sample gas 8 to be introduced. The second end of the separation column 1 is connected to a detector 10, which is likewise provided in a recess in the plate 11. With the aid of this detector, it is possible to assess the sample gas 8 which is to be analyzed, which gas is for example natural gas.

Figure 4:
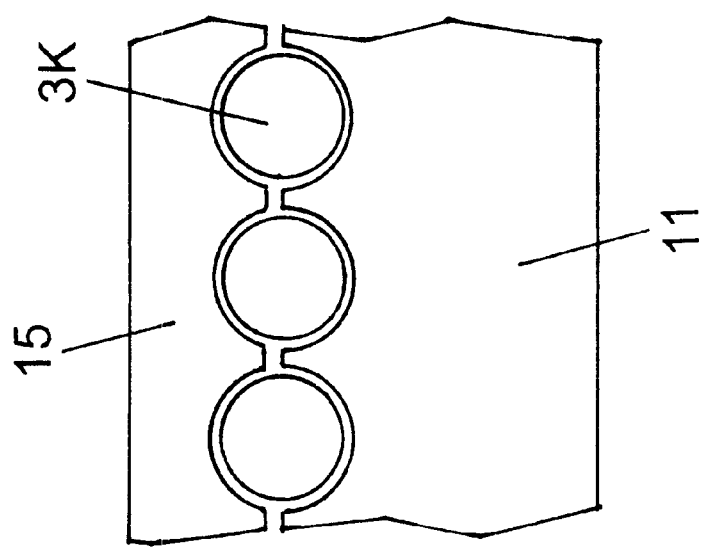
FIG. 4 is a diagrammatic, partial sectional view of a further embodiment of a separation column according to the invention which is integrated in a support element.

FIG. 4 is a diagrammatic, partial sectional view of a further embodiment of a separation column wherein the channel 13 is formed partially in the surface 11S of the plate 11 and partially in the cover 15. In this case, the plate 11 and the cover 15 are provided with a deeper recess at the locations at which each sphere 3K is to be provided. After the cover 15 has been connected to the plate 11 in a gastight manner, a separation column formed in this way has the same properties as a separation column formed only in the surface of the plate 11. This separation column also has the same dimensions.

We claim:

1. A separation column for analyzing gases, comprising:
   a capillary having an inner diameter being substantially 200 μm;
   spheres having substantially identical diameters, said spheres being disposed as a separation material in said capillary, said substantially identical diameters of said spheres being between 150 vim and 200 μm.

2. The separation column according to claim 1, wherein said spheres are formed of carbon.

3. The separation column according to claim 1, wherein said spheres are formed of Carbosphere carbon.

4. The separation column according to claim 1, wherein said capillary has two ends, and a respective gas-permeable closure is provided at each of said two ends of said capillary.

5. The separation column according to claims 1, including:
   two further capillaries having respective inner diameters and respective outer diameters, said inner diameters of said two further capillaries being smaller than said substantially identical diameters of said spheres, said outer diameters of said two further capillaries being matched to said inner diameter of said capillary; and
   said capillary having two ends, said two further capillaries each having a respective first end inserted in a respective one of said two ends of said capillary, said two further capillaries being connected to said capillary in a gastight and permanent manner such that said two further capillaries form gas-permeable closures at said two ends of said capillary.

6. The separation column according to claim 1, including:
   a support element including a plate and a cover, said plate and said cover being made from a material selected from the group consisting of glass and silicon;
   said plate having a surface and having a channel formed in said surface, said channel having relatively wider sections for receiving said spheres and said channel having relatively narrower sections in front of and behind each of said relatively wider sections; and
   said cover closing off said channel in a gastight manner with respect to an outside environment for providing said capillary, said channel having an end serving as an inlet opening for a carrier gas and a sample gas.

7. The separation column according to claim 1, including:
   a support element including a plate and a cover, said plate and said cover being made from a material selected from the group consisting of glass and silicon;

said plate and said cover having respective surfaces facing one another and having a channel formed partially in each of said surfaces, said channel having relatively wider sections for receiving said spheres and said channel having relatively narrower sections in front of and behind each of said relatively wider sections; and said cover closing off said channel in a gastight manner with respect to an outside environment for providing said capillary, said channel having an end serving as an inlet opening for a carrier gas and a sample gas.

8. A separation column for analyzing gases, comprising:

a capillary having an inner diameter;

spheres having substantially identical diameters, said spheres being disposed as a separation material in said capillary, said spheres having respective center points, said spheres being disposed inside said capillary such that all of said center points of said spheres are provided along a straight line;

each of said substantially identical diameters of said spheres being selected from the group consisting of a diameter matched to said inner diameter of said capillary and a diameter marginally smaller than said inner diameter of said capillary.

9. A separation column for analyzing gases, comprising:

a capillary having an inner diameter;

spheres having substantially identical diameters, said spheres being disposed as a separation material in said capillary, each of said substantially identical diameters of said spheres being selected from the group consisting of a diameter matched to said inner diameter of said capillary and a diameter marginally smaller than said inner diameter of said capillary; and an inert powder provided between said spheres at least in given regions inside said capillary.

10. The separation column according to claim 9, wherein said inert powder is made from a material selected from the group consisting of carbon, Buckminister Fullerene C60 and Carbosphere carbon.

* * * * *